United States Patent
Prasad et al.

(10) Patent No.: US 7,605,145 B2
(45) Date of Patent: *Oct. 20, 2009

(54) MICRONUTRIENT FORMULATIONS FOR TREATMENT OF DIABETES MELLITUS

(75) Inventors: Kedar N. Prasad, Novato, CA (US); William C. Cole, Novato, CA (US); Gerald M. Haase, Greenwood Village, CO (US)

(73) Assignee: Premier Micronutrient Corporation, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/943,176

(22) Filed: Nov. 20, 2007

(65) Prior Publication Data

US 2008/0118488 A1 May 22, 2008

Related U.S. Application Data

(60) Provisional application No. 60/866,462, filed on Nov. 20, 2006.

(51) Int. Cl.
| | |
|---|---|
| *A61K 31/714* | (2006.01) |
| *A61K 31/59* | (2006.01) |
| *A61K 31/555* | (2006.01) |
| *A61K 31/525* | (2006.01) |
| *A61K 31/51* | (2006.01) |

(52) U.S. Cl. .......... 514/52; 514/251; 514/184; 514/393; 514/350; 514/167

(58) Field of Classification Search .......... None
See application file for complete search history.

(56) References Cited

U.S. PATENT DOCUMENTS

| | | | | | |
|---|---|---|---|---|---|
| 5,292,538 | A | * | 3/1994 | Paul et al. | 426/74 |
| 5,561,160 | A | * | 10/1996 | Walaszek et al. | 514/574 |
| 5,626,883 | A | * | 5/1997 | Paul | 424/605 |
| 5,895,652 | A | * | 4/1999 | Giampapa | 424/195.17 |
| 5,976,568 | A | * | 11/1999 | Riley | 424/451 |
| 6,245,360 | B1 | * | 6/2001 | Markowitz | 424/641 |
| 6,291,533 | B1 | * | 9/2001 | Fleischner | 514/682 |
| 6,667,063 | B2 | * | 12/2003 | Crum | 424/535 |
| 6,686,340 | B2 | * | 2/2004 | Rath | 514/52 |
| 6,849,613 | B2 | * | 2/2005 | Prasad et al. | 514/52 |
| 7,399,755 | B2 | * | 7/2008 | Prasad et al. | 514/52 |
| 2003/0064955 | A1 | * | 4/2003 | Prasad et al. | 514/52 |
| 2003/0147996 | A1 | * | 8/2003 | Prasad et al. | 426/74 |

* cited by examiner

*Primary Examiner*—Brian-Yong S Kwon
(74) *Attorney, Agent, or Firm*—Dan DeLa Rosa

(57) ABSTRACT

Formulations for minimizing damage to at least one of cells, organs and systems within the body of a subject afflicted with Diabetes Mellitus. The invention additionally encompasses methods for minimizing said damage which comprise administering to subjects in need thereof a therapeutic amount of a formulation(s) according to the invention.

3 Claims, No Drawings

MICRONUTRIENT FORMULATIONS FOR TREATMENT OF DIABETES MELLITUS

TECHNICAL FIELD

The invention relates to multiple antioxidant formulations useful in the management of Diabetes Mellitus.

BACKGROUND OF THE INVENTION

Diabetes Mellitus has become a serious national health problem that has reached epidemic proportions. In the year 2000, for example, the Centers for Disease Control and Prevention reported that 16 million Americans, i.e., 5.4% of the total national population, were known to suffer from diabetes. They additionally estimated that another 5.5 million people with the disease were as yet undiagnosed.

The major types of diabetes include insulin-dependent and insulin-independent varieties. In the so-called "type I" diabetes, there is a primary loss of insulin secretion related to either deficiency, destruction or inactivity of pancreatic beta cells. In "type II" diabetes, there may be adequate insulin secretion, but there is a varying degree of insulin resistance in the peripheral target tissues. Therefore, the cells respond as if there is inadequate insulin present. The incidence of type II diabetes is known to be increasing in the U.S. military veteran population. Of about 3.2 million veterans who have utilized the Veterans Administration health care system, almost 555,000 were for the care of diabetes, at an annual cost of more than four billion dollars.

The most important clinical issues regarding diabetes and its appropriate control revolve around the disease complications rather than the abnormality in serum glucose itself. The most important complications involve diseases of small blood vessels—specifically in relation to cardiovascular disease, polyneuropathy, proliferative retinopathy and renal vascular disease.

It appears that most of the complications induced by adult onset diabetes (such as polyneuropathy or cataract formation) are related to excess free radicals and oxidative stress. Therefore, it is plausible that the use of multiple antioxidants may be beneficial in reducing these disease-related complications. For example, natural alpha lipoic acid and its metabolite dihydroxy lipoic acid have been shown to prevent many of the biologic changes induced by diabetes. It has also been shown that alpha lipoic acid reduces chemically induced diabetes in animal models by 50%.

It has further been proposed that the experimental findings noted above have as their foundation the involvement of nitric oxide, a nitrogen derived free radical and other reactive oxygen species. Therefore, it becomes increasingly rational that multiple antioxidants including alpha lipoic acid will be beneficial in the prevention and treatment of type I diabetes. It is likely that the mechanism of this action will involve some degree of protection of the pancreatic beta cells against free radical damage from excess oxidative stress.

In type II diabetes, the major problem is insulin resistance in the target tissues. Alpha lipoic acid can benefit this situation by improving glucose utilization in peripheral tissue by stimulating glucose transport and uptake. Additionally, the glycation of proteins has been identified as a possible factor responsible for other complications associated with diabetes. In a similar beneficial manner alpha lipoic acid has been shown to reduce this protein enzyme effect.

In light of the considerations set forth above, therefore, there has been a long-felt need by those working in this field for an antioxidant-based formulation capable of reducing, if not entirely overcoming the above-described obstacles to the management of Diabetes Mellitus.

SUMMARY OF THE INVENTION

In one embodiment, the invention provides a formulation for minimizing damage to at least one of cells, organs and systems within the body of a subject afflicted with Diabetes Mellitus, wherein the damage is caused by or is associated with the presence or progress of the disease. The formulation comprises

| | |
|---|---|
| vitamin A (palmitate) | 3,000-5000 I.U. |
| beta-carotene (from natural *d. salina*) | 10-20 mg |
| vitamin D-3 (cholecalciferol) | 200-600 I.U. |
| natural source vitamin E | 100-400 I.U. |
| (d-alpha tocopherol succinate) | 400 I.U. |
| (d-alpha tocopheryl acetate) | 100 I.U. |
| vitamin C (calcium ascorbate) | 100-2000 mg |
| thiamine mononitrate | 1-10 mg |
| riboflavin | 1-20 mg |
| niacinamide ascorbate | 10-60 mg |
| d-calcium pantothenate | 5-30 mg |
| pyridoxine hydrochloride | 1-10 mg |
| cyanocobalamin | 5-30 mcg |
| folic acid (folacin) | 400-1600 mcg |
| d-biotin | 100-1600 mcg |
| selenium (I-seleno-methionine) | 100-250 mcg |
| chromium picolinate | 50-250 mcg |
| zinc glycinate | 10-60 mg |
| calcium citrate | 100-500 mg |
| magnesium citrate | 50-250 mg |
| n-acetyl cysteine | 100-500 mg |
| alpha lipoic acid | 50-200 mg |
| co-enzyme $Q_{10}$ | 10-200 mg |
| L-carnitine | 100-400 mg |

In another embodiment, the invention comprises a method for minimizing damage to at least one of cells, organs and systems within the body of a subject afflicted with Diabetes Mellitus. The method comprises administering to the subject a therapeutic amount of a formulation for minimizing such damage. The formulation comprises:

| | |
|---|---|
| vitamin A (palmitate) | 3,000-5000 I.U. |
| beta-carotene (from natural *d. salina*) | 10-20 mg |
| vitamin D-3 (cholecalciferol) | 200-600 I.U. |
| natural source vitamin E | 100-400 I.U. |
| (d-alpha tocopherol succinate) | 400 I.U. |
| (d-alpha tocopheryl acetate) | 100 I.U. |
| vitamin C (calcium ascorbate) | 100-2000 mg |
| thiamine mononitrate | 1-10 mg |
| riboflavin | 1-20 mg |
| niacinamide ascorbate | 10-60 mg |
| d-calcium pantothenate | 5-30 mg |
| pyridoxine hydrochloride | 1-10 mg |
| cyanocobalamin | 5-30 mcg |
| folic acid (folacin) | 400-1600 mcg |
| d-biotin | 100-1600 mcg |
| selenium (I-seleno-methionine) | 100-250 mcg |
| chromium picolinate | 50-250 mcg |
| zinc glycinate | 10-60 mg |
| calcium citrate | 100-500 mg |
| magnesium citrate | 50-250 mg |
| n-acetyl cysteine | 100-500 mg |
| alpha lipoic acid | 50-200 mg |
| co-enzyme $Q_{10}$ | 10-200 mg |
| L-carnitine | 100-400 mg |

DETAILED DESCRIPTION OF THE INVENTION

A multiple antioxidant mixture such as that used in the management of Diabetes Mellitus must be based on a rational formulation including aqueous and lipid-soluble substances, selected minerals, and B vitamins in optimal relative proportions. For complex patients with adult onset diabetes there should also be increased levels of vitamin C, d-alpha tocopheryl succinate, N-acetyl cysteine, co-enzyme $Q_{10}$, and alpha lipoic acid. Vitamin research demonstrates that less than ten percent of oral supplementation is absorbed and the half-life of water-soluble constituents is six hours, while that of lipid-soluble constituents is eight hours. Therefore, administration of an antioxidant micronutrient formulation according to the invention twice a day is necessary to ensure consistently high levels of antioxidants.

In general the class of micronutrients to which the components of the present formulation(s) belong is known to stimulate the immune system, reduce the formation of toxic chemicals in the body and prevent activation of cancer-causing substances in the liver. Specifically as related to diabetes mellitus, the subject antioxidants protect pancreatic cells from the injurious effects of multiple species of free radicals. The high level of various types of free radicals produced in this clinical situation mandates that a multiple antioxidant mixture be utilized for optimal effect.

Recent studies suggest that beta-carotene does not only act as a precursor of vitamin A as previously thought. In fact, it is now known that both of these substances are individually necessary in micronutrient supplementation. Vitamin A is critical in cell differentiation induction while beta-carotene increases the expression of tumor suppressor genes and is more efficient in quenching free radicals. It has thus been determined by the inventors that a formulation in patients receiving supplements should utilize a natural form of both of these antioxidants.

It is also known that not all forms of vitamin E are equally soluble or can enter the cells easily. Alpha tocopherol is most important to protect the extracellular environment from free radicals while d-alpha tocopheryl succinate is most effective in maintaining internal cellular components. Both forms are necessary to optimize vitamin E function in this clinical situation. In addition, the non-acidic form of vitamin C should be utilized especially with the slightly increased dosage necessary in this high-risk population.

Finally, it is well known that minerals such as iron, copper and manganese when combined with vitamin C generate excess free radicals. This pro-oxidative state enhances cell injury and is exactly the opposite of what would be desired for a patient with diabetes mellitus and small vessel damage. In general, iron administration should always be undertaken cautiously since its absorption is dramatically increased in the presence of a high antioxidant environment and inappropriate total body iron stores have a deleterious effect on many chronic diseases such as diabetes.

The formulations and methods according to the invention are as described below.

| | |
|---|---|
| vitamin A (palmitate) | 3,000-5000 I.U. |
| beta-carotene (from natural *d. salina*) | 10-20 mg |
| vitamin D-3 (cholecalciferol) | 200-600 I.U. |
| natural source vitamin E | 100-400 I.U. |
| (d-alpha tocopherol succinate) | 400 I.U. |
| (d-alpha tocopheryl acetate) | 100 I.U. |
| vitamin C (calcium ascorbate) | 100-2000 mg |
| thiamine mononitrate | 1-10 mg |
| riboflavin | 1-20 mg |
| niacinamide ascorbate | 10-60 mg |
| d-calcium pantothenate | 5-30 mg |

-continued

| | |
|---|---|
| pyridoxine hydrochloride | 1-10 mg |
| cyanocobalamin | 5-30 mcg |
| folic acid (folacin) | 400-1600 mcg |
| d-biotin | 100-1600 mcg |
| selenium (I-seleno-methionine) | 100-250 mcg |
| chromium picolinate | 50-250 mcg |
| zinc glycinate | 10-60 mg |
| calcium citrate | 100-500 mg |
| magnesium citrate | 50-250 mg |
| n-acetyl cysteine | 100-500 mg |
| alpha lipoic acid | 50-200 mg |
| co-enzyme $Q_{10}$ | 10-200 mg |
| L-carnitine | 100-400 mg |

For women 40 years of age and older, the following supplements should be added to the above-described formulation:

| | |
|---|---|
| calcium citrate | 1000-2000 mg |
| magnesium citrate | 500-1000 mg |
| vitamin D | 50-150 I.U. |

In a preferred embodiment of the invention the formulation comprises:

| | |
|---|---|
| vitamin A (palmitate) | 5,000 I.U. |
| beta-carotene (from natural *d. salina*) | 15 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| vitamin C (calcium ascorbate) | 1,500 mg |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 mcg |
| folic acid (folacin) | 800 mcg |
| d-biotin | 200 mcg |
| selenium (I-seleno-methionine) | 150 mcg |
| chromium picolinate | 150 mcg |
| zinc glycinate | 15 mg |
| calcium citrate | 250 mg |
| magnesium citrate | 125 mg |
| n-acetyl cysteine | 300 mg |
| alpha lipoic acid | 100 mg |
| co-enzyme $Q_{10}$ | 90 mg |
| L-carnitine | 200 mg |

For women 40 years of age and older, the following supplements should be added to the above-described formulation:

| | |
|---|---|
| calcium citrate | 1,500 mg |
| magnesium citrate | 750 mg |
| vitamin D | 100 I.U. |

The above-described formulations are typically administered orally to a subject in need thereof, i.e., for the purpose of mitigating, if not entirely eliminating, the symptoms of Diabetes Mellitus. In a preferred manner of administration, the formulations are packaged into 4 to 6 #00 size capsules, which comprise, in toto, a typical complete daily dosage. In order to maintain proper serum levels of the various antioxidants and vitamin substances, the total dosage may be split in half, i.e., with half of the total capsules being administered at one time of day and the other half approximately twelve (12) hours later, e.g., with the first administration typically occurring in the morning and the second occurring about half a day later in the evening.

It should also be understood that, in addition to administration of formulations comprised of antioxidant micronutrients in accordance with the invention, following diet and lifestyle recommendations from one's healthcare professional are also very important in minimizing the effects of Diabetes Mellitus. For example, as to the diet, one should consume a balanced diet. Several smaller meals/snacks throughout the day are more desirable than one or two large meals. One should also increase the amount of fiber intake in one's diet, especially from fruits and vegetables. Between meals, one should avoid sweetened or artificially sweetened drinks. In addition, consumption of chewing gum and/or candy, as well as that of alcoholic beverages, should to limited to mealtime so as to minimize the amounts consumed. Additionally, starch-heavy foods and/or sweets should be limited to mostly one meal during the day.

Additionally, one should not smoke or chew tobacco and regulate caffeine intake. If possible, one should adopt a lifestyle wherein stress is reduced to the degree possible and which involves regular exercise, i.e., preferably 3 to 5 days a week for at least thirty minutes.

What is claimed is:

1. A formulation consisting of:

| | |
|---|---|
| vitamin A (palmitate) | 3,000-5000 I.U. |
| beta-carotene (from natural *d. salina*) | 10-20 mg |
| vitamin D-3 (cholecalciferol) | 200-600 I.U. |
| natural source vitamin E | |
| (d-alpha tocopherol succinate) | 100-400 I.U. |
| (d-alpha tocopheryl acetate) | 100-400 I.U. |
| vitamin C (calcium ascorbate) | 100-2000 mg |
| thiamine mononitrate | 1-10 mg |
| riboflavin | 1-20 mg |
| niacinamide ascorbate | 10-60 mg |
| d-calcium pantothenate | 5-30 mg |
| pyridoxine hydrochloride | 1-10 mg |
| cyanocobalamin | 5-30 mcg |
| folic acid (folacin) | 400-1600 mcg |
| d-biotin | 100-1600 mcg |
| selenium (I-seleno-methionine) | 100-250 mcg |
| chromium picolinate | 50-250 mcg |
| zinc glycinate | 10-60 mg |
| calcium citrate | 100-500 mg |
| magnesium citrate | 50-250 mg |
| n-acetyl cysteine | 100-500 mg |
| alpha lipoic acid | 50-200 mg |
| co-enzyme Q10 | 10-200 mg |
| L-carnitine | 100-400 mg |

Said formulation is designed for the treatment of Diabetes Mellitus.

2. The formulation of claim 1 wherein said formulation is consumed by a user at least twice per day.

3. The formulation of claim 1 wherein said formulation is consumed is from about at least one week to about life long.

* * * * *